(12) United States Patent
Wei et al.

(10) Patent No.: US 8,205,991 B2
(45) Date of Patent: Jun. 26, 2012

(54) METHOD OF EYE REGISTRATION FOR OPTICAL COHERENCE TOMOGRAPHY

(75) Inventors: Jay Wei, Fremont, CA (US); Ben Kwei Jang, Cupertino, CA (US); Shuw-Shenn Luh, Fremont, CA (US); Yuanmu Deng, Fremont, CA (US)

(73) Assignee: Optovue, Inc., Fremont, CA (US)

( * ) Notice: Subject to any disclaimer, the term of this patent is extended or adjusted under 35 U.S.C. 154(b) by 519 days.

(21) Appl. No.: 12/423,757

(22) Filed: Apr. 14, 2009

(65) Prior Publication Data

US 2009/0257636 A1 Oct. 15, 2009

Related U.S. Application Data

(60) Provisional application No. 61/124,109, filed on Apr. 15, 2008.

(51) Int. Cl.
*A61B 3/00* (2006.01)

(52) U.S. Cl. .......................................... 351/246; 382/128

(58) Field of Classification Search .................. 382/128; 351/200, 204, 205, 246
See application file for complete search history.

(56) References Cited

U.S. PATENT DOCUMENTS

| | | | |
|---|---|---|---|
| 7,480,058 B2 | 1/2009 | Zhao et al. | |
| 7,593,559 B2 * | 9/2009 | Toth et al. | 382/128 |
| 7,744,221 B2 | 6/2010 | Wei et al. | |
| 7,924,429 B2 * | 4/2011 | Knighton et al. | 356/479 |
| 2004/0042022 A1 * | 3/2004 | Friedman et al. | 358/1.9 |
| 2004/0263785 A1 | 12/2004 | Chernyak | |
| 2006/0115110 A1 * | 6/2006 | Rodriguez et al. | 382/100 |
| 2006/0187462 A1 * | 8/2006 | Srinivasan et al. | 356/479 |
| 2007/0115481 A1 | 5/2007 | Toth et al. | |
| 2008/0267515 A1 * | 10/2008 | Harrington | 382/233 |
| 2008/0310757 A1 * | 12/2008 | Wolberg et al. | 382/285 |
| 2009/0268161 A1 * | 10/2009 | Hart et al. | 351/208 |
| 2010/0030578 A1 * | 2/2010 | Siddique et al. | 705/3 |
| 2010/0245838 A1 * | 9/2010 | Everett et al. | 356/497 |
| 2011/0085136 A1 * | 4/2011 | Ferguson et al. | 351/206 |
| 2011/0134394 A1 * | 6/2011 | Srinivasan et al. | 351/246 |
| 2011/0194072 A1 * | 8/2011 | Olivier et al. | 351/206 |

FOREIGN PATENT DOCUMENTS

| | | |
|---|---|---|
| WO | WO 01/78584 A2 | 10/2001 |
| WO | WO 2006/078802 A1 | 7/2006 |
| WO | WO 2007/084748 A2 | 7/2007 |

OTHER PUBLICATIONS

PCT International Search Report and the Written Opinion mailed Aug. 31, 2009, in related International Application No. PCT/US2009/002343.
PCT International Preliminary Report on Patentability dated Oct. 28, 2010, in related International Appl. No. PCT/US2009/002343.

* cited by examiner

*Primary Examiner* — Nathan Ha
(74) *Attorney, Agent, or Firm* — Haynes and Boone, LLP (57) ABSTRACT

A method is disclosed for use in eye registrations and examinations, some embodiments of the method including acquiring scan pattern scans; forming images from the scans; registering the images; generating a feature map from the scan pattern scans; identifying features on the feature map; and recording positional information of features.

21 Claims, 11 Drawing Sheets

METHOD OF EYE REGISTRATION FOR OPTICAL COHERENCE TOMOGRAPHY

RELATED APPLICATION

The present application claims priority to provisional application No. 61/124,109, entitled "Method of Eye Registration for Optical Coherence Tomography," filed on Apr. 15, 2008, which is herein incorporated by reference in its entirety.

BACKGROUND

1. Field of the Invention

The present invention is related to a method of performing eye examinations and, in particular, a method of performing an eye registration utilizing optical coherence tomography (OCT).

2. Discussion of Related Art

Optical coherence tomography is increasingly becoming an important tool in non-invasive human eye retinal imaging. Use of OCT for imaging the anterior has shown great promise for detection and analysis of refractive problems, cataracts, and glaucoma, among other issues. However, eye motion renders comparison of subsequent images difficult.

Therefore, there is a need for imaging procedures that allow accurate comparisons of OCT scan images over time.

SUMMARY

Consistent with the present invention, a method according to some embodiments of the present invention includes acquiring scan pattern scans; forming images from the scans; registering the images; generating a feature map from the scan pattern scans; identifying features on the feature map; and recording positional information of features.

In some embodiments of the invention, registering the image can include generating a patch image and matching the patch image with a baseline image. In some embodiments, registering the image can include generating a simulated scanning laser ophthalmoscope (SSLO) image and matching the SSLO image with a previously taken SSLO image.

These and other embodiments are further described below with respect to the following figures.

Wherever possible, elements having the same or similar function have the same designation.

DETAILED DESCRIPTION

Figure 1:
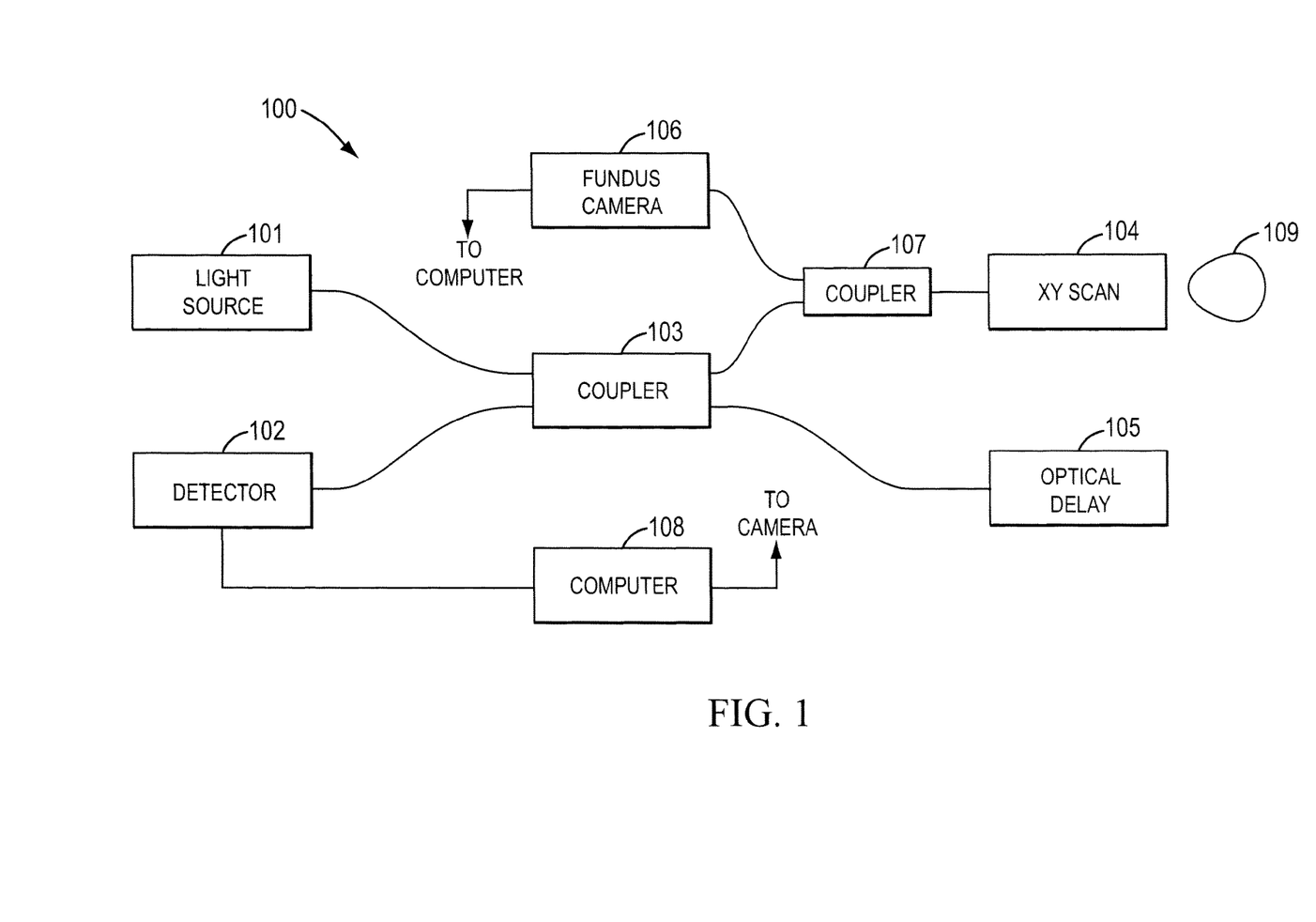
FIG. 1 illustrates an OCT scanner that can be utilized consistently with some embodiments of the present invention.

FIG. 1 illustrates an example of an OCT imager 100 that can be utilized in eye examinations according to some embodiments of the present invention. OCT imager 100 includes light source 101 supplying light to coupler 103, which directs the light through the sampling arm to XY scan 104 and through the reference arm to optical delay 105. XY scan 104 scans the light across eye 109 and collects the reflected light from eye 109. Light reflected from eye 109 is captured in XY scan 104 and combined with light reflected from optical delay 105 in coupler 103 to generate an interference signal. The interference signal is coupled into detector 102. OCT imager 100 can be a time domain OCT imager, in which case depth (or A-scans) are obtained by scanning optical delay 105, or a Fourier domain imager, in which case detector 102 is a spectrometer that captures the interference signal as a function of wavelength. In either case, the OCT scans are captured by computer 108. Collections of scans taken along an XY pattern are utilized to generate OCT images. An example of an OCT imager is described in U.S. Pat. No. 7,480,058, which is herein incorporated by reference in its entirety. A method of Eye Examination utilizing an OCT imager is disclosed in U.S. application Ser. No. 11/656,075, which is herein incorporated by reference in its entirety.

In addition to the OCT imager 100, an apparatus for eye examinations according to the present invention can include a camera 106, which can be a fundus camera. Light from camera 106 is coupled into the sample arm of OCT imager 100 by a coupler 107. Coupler 107 prevents light from camera 106 from entering coupler 103 while directing reflected light from eye 109 that originates from camera 106 back into camera 106. Computer 108 receives and analyzes both the images from camera 106 and the images from OCT imager 100. Utilizing the combination of images, accurate and complete OCT images of the nerve head can be obtained.

Figure 2A:
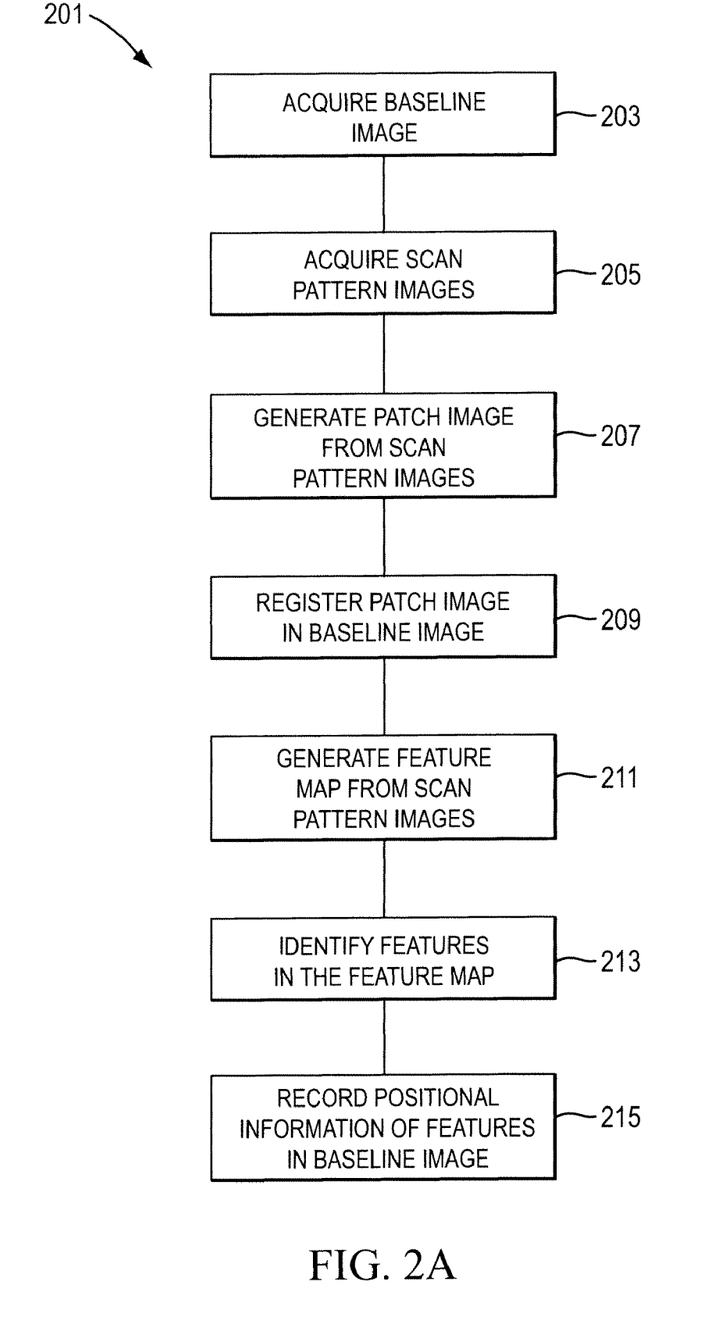
FIGS. 2A and 2B illustrate some embodiments of procedures for eye registration and feature recognition consistent with the present invention.

FIG. 2A illustrates a procedure for performing eye registration and analysis according to some embodiments of the present invention. In some embodiments of the invention, an automated method and apparatus to perform the eye registration based on two-dimensional (2D) or three-dimensional (3D) OCT images can be performed on computer 108 for display on a monitor or other interface device. The 2D fundus video image, which does not include depth information, is obtained at the output of the fundus camera 106. In contrast, OCT images, which do include depth information, are output from detector 102 and are composed or arranged, depending on their scan patterns, to display as a 2D enface image or a 3D volume data, as desired for a particular evaluation. In some embodiments, scan data is stored on computer 108 for subsequent analysis. A fundus image from fundus camera 106 may also be stored on computer 108. In some embodiments of the invention, the parameters of subsequent image processing techniques may be calculated more robustly and efficiently, leading to better accurate diagnosis by physicians.

Procedure 201 shown in FIG. 2A is a process for registering and analyzing images that is consistent with some embodiments of the present invention. In step 203, a baseline image is acquired and saved, if that image has not already been obtained. In step 205, scan pattern images are acquired. Scan pattern images may include feature scans and patch scans. In step 207 a patch image is formed from the patch scans. In step 209, the patch image is registered against the baseline image. In step 211 a feature map is generated from the feature scans. In step 213, the features in the feature map are identified. In step 215, positional information of features from the feature map are recorded. As a result of this procedure, the patch image is precisely located within the baseline image, regardless of whether the eye has moved or individual blood vessels or other features have changed. Features are then identified and located precisely with respect to the baseline image in order to monitor changes in feature positions and other attributes.

Figure 2B:
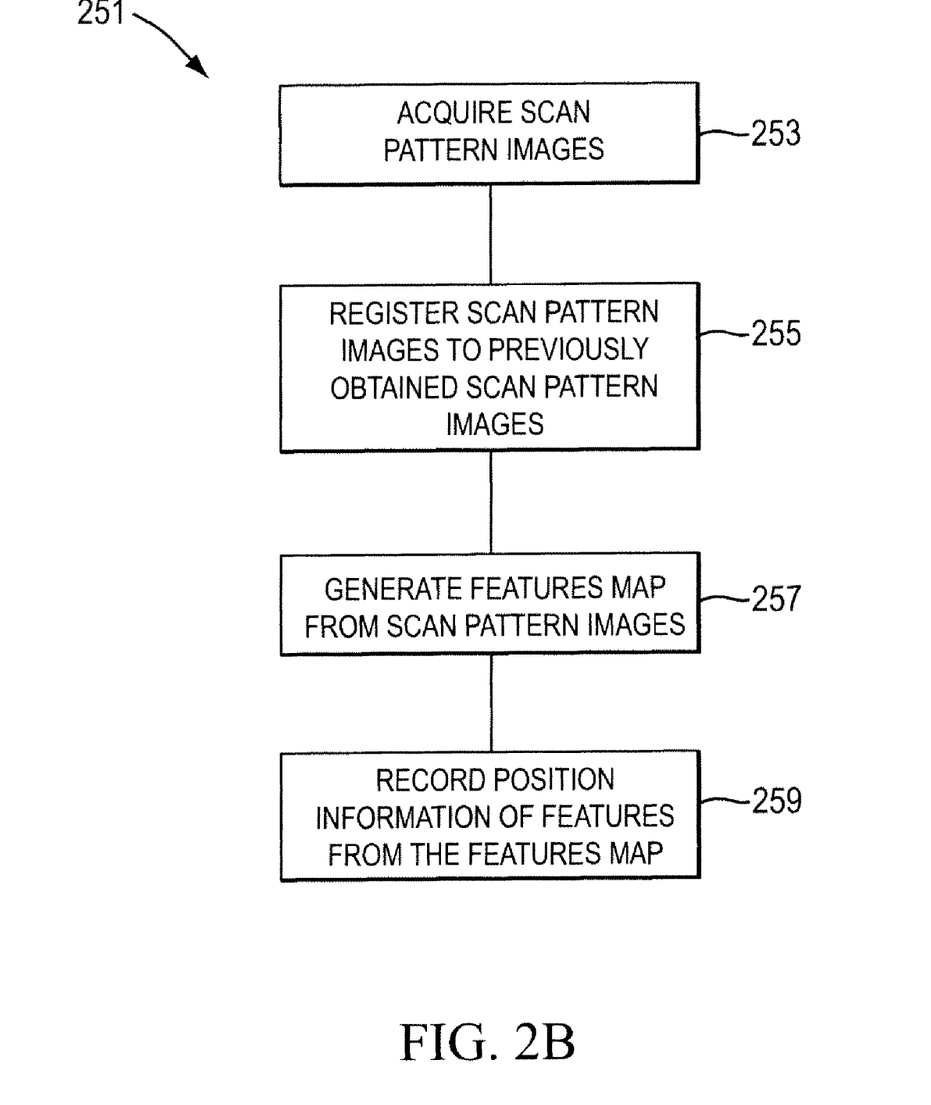

Procedure 251 shown in FIG. 2B shows another procedure for registering and analyzing images consistently with the present invention. As shown in FIG. 2B, scan pattern images are acquired in step 253. The scan pattern images include original feature scans and additional feature scans. In step 255, the scan pattern images are registered with respect to previously obtained scan pattern images. In step 257, a features map is generated from the scan pattern images. Finally, in step 259, position information for features identified in the features map is recorded. The position and condition of features identified can then be tracked over time in a precise fashion.

In some embodiments, images from other modalities may be taken simultaneously with the OCT images, for example the 2D fundus video image taken by fundus camera 106 in FIG. 1. The 3D OCT images acquired according to some embodiments of the present invention can perform well in the presence of eye motion and blood vessel displacement that may occur during the scans.

As described above, some embodiments of the present invention can be utilized for more accurate evaluating the eye tissue structure for diagnosing eye diseases. An enface image, like a fundus image, can be composed by summing the tissue reflectivity of a sequence OCT images. An algorithm to register and map out the eye tissue structure accurately then provides for accurate location of features and tracking of changes of those features over time. Eye registration methods according to some embodiments of the present invention can be utilized in the diagnoses of eye pathologies in the fovea, for example Diabetic Retinopathy. These methods can also be utilized in the diagnoses of eye pathologies in the optic nerve head, for example Glaucoma.

Figure 3:
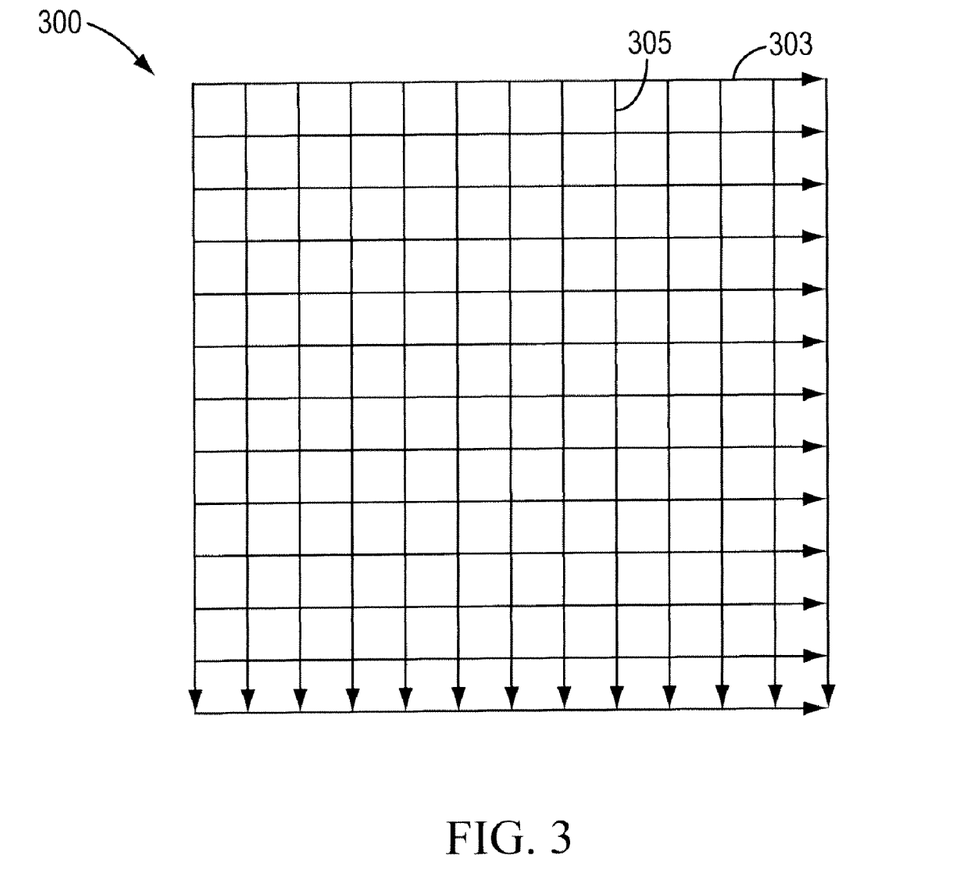
FIG. 3 illustrates an example of a scan pattern for acquiring a series of OCT images.

As shown in step 203 of FIG. 2A, some embodiments utilize a baseline image upon which the registration is performed as in step 209. The baseline image can be saved and utilized for further studies, for example a progressive analysis. FIG. 3 shows an example of baseline scan pattern 300 that can be utilized to acquire a sequence of OCT images. Scan pattern 300, which in this case includes horizontal scans 303 and vertical scans 305, can be arranged to substantially cover the eye features of interest, for example, the fovea or optic nerve head.

Figure 4:
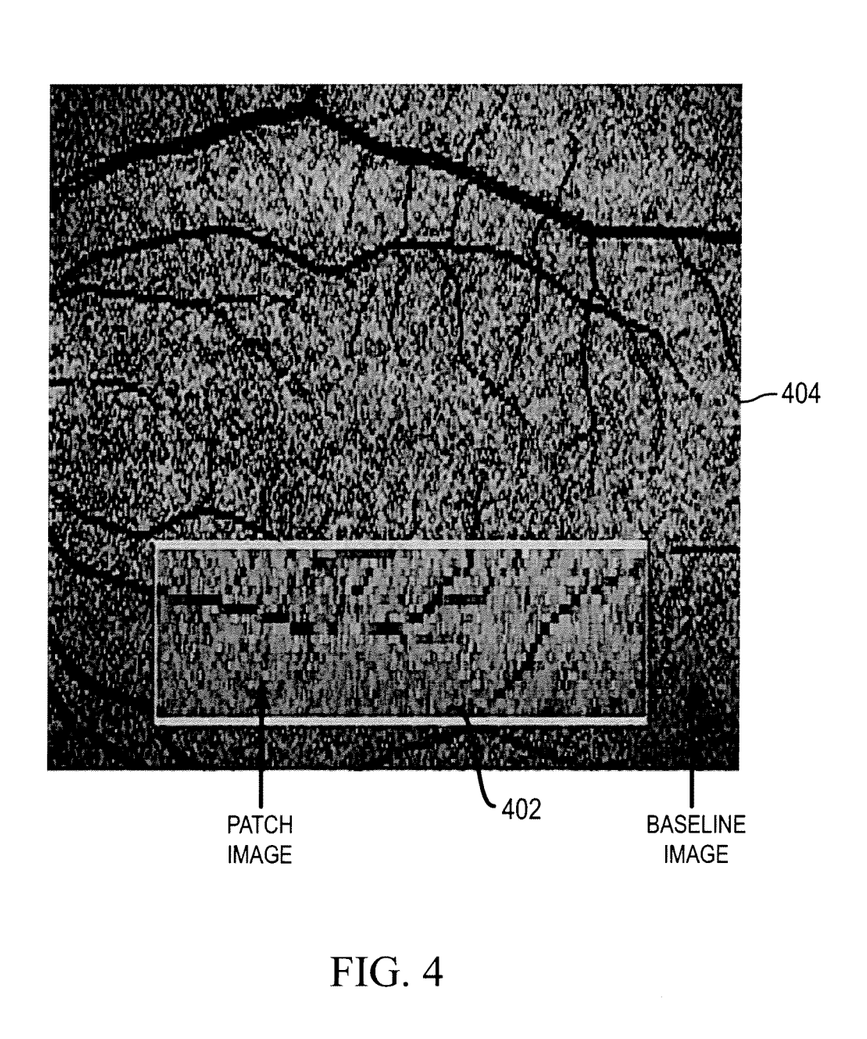
FIG. 4 illustrates registration of a sample patch image within a sample baseline image.

The baseline image is then generated from scan pattern 300, similar to the generation of an enface image, by summing all or partial tissue reflectivity of the scanned OCT images. A baseline image 404 formed in such a fashion is shown in FIG. 4. FIG. 4 shows registration of a sample patch image 402 within a sample baseline image 404. Baseline image 404 is generated from a baseline scan pattern such as baseline scan pattern 300. Patch image 402 is generated from patch scans. As can be seen from FIG. 4, features such as the retinal blood vessels in baseline image 404 can be enhanced and can be utilized as landmarks to help in registering patch image 402. Other features may also be utilized, such as retinal thicknesses.

Figure 5:
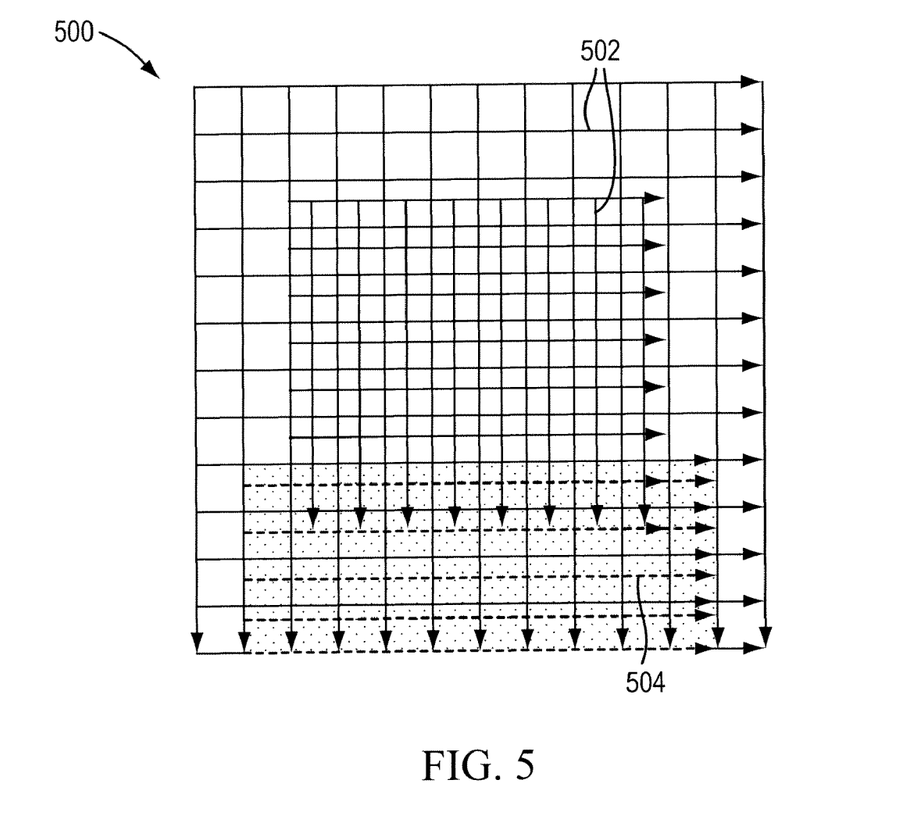
FIG. 5 shows a scan pattern to acquire a sequence of OCT images that includes feature scans and patch scans that can be utilized for registration.

FIG. 5 shows a scan pattern 500 that can be utilized to generate a sequence of OCT images. Scan pattern 500 includes feature scans 502 denoted by solid lines and patch scans 504 denoted by broken lines. As indicated in step 211 of procedure 201 of FIG. 2A, a feature map can be generated from feature scans 502. Further, as indicated in step 207, a patch image such as patch image 402 can be generated from patch scans 504 and used for registration with baseline image 404 in step 209.

Retinal thickness, measured from the inner limiting membrane (ILM) to the retinal pigment epithelium (RPE), can be used as a feature and is a useful illustration because it is an important consideration in the assessment of many macular diseases. Retinal thickness may be increased with edema, which can have a profound effect on visual acuity. The accumulation of intra-retinal fluid will lead to both an increased retinal thickness, and also a change in the scattering properties of the retinal tissue, which is detectable in an OCT scan.

Figure 6:
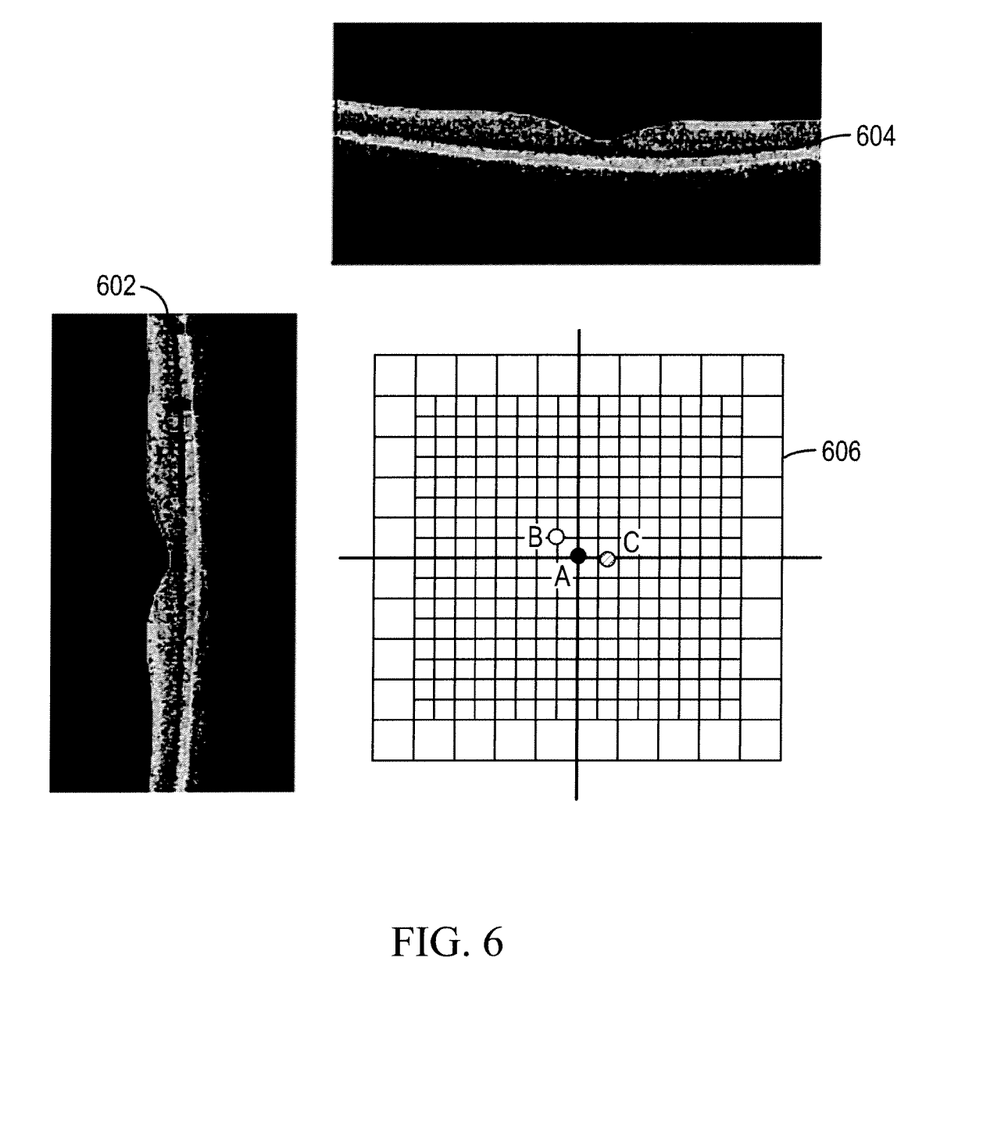
FIG. 6 shows a schematic illustrating generating a feature map, identifying features on the feature map, and recording positional information of features consistent with some embodiments of the present invention.

FIG. 6 shows a schematic picture illustrating generation of a feature map, which is accomplished in step 211 of FIG. 2A, identifying features in the feature map, and recording the positional information of features as in steps 211 through 215 of procedure 201. As shown in FIG. 6, a vertical retinal thickness scan 602 and a horizontal thickness scan 604 are shown. An important location to measure retinal thickening is directly in the fovea, as indicated with the two thinning areas in thickness scans 602 and 604. The location of that point is shown as point C of feature map 606. This type of measurement can be particular useful in tracking patients with macular edema due to diabetic retinopathy, or for screening and following patients with cystoid macular edema following cataract surgery. On the other hand, retinal thickness may be decreased with atrophy or scattering. Retinal thickness map 606 is an example of a feature map for illustrative purposes. Other features besides retinal thickness may also be monitored and utilized in the feature map.

A patch image such as patch image 402 can be generated from a patch scan similar to generation of the baseline image as described above. A feature map such as feature map 606 is generated from feature scans 502 of FIG. 5 using a 2D interpolation technique. In feature map 606 shown in FIG. 6, point A indicates the aiming center of scan pattern 500, point B the aiming center of baseline scan pattern 300, and point C a feature location, which in FIG. 6 is the fovea as shown in scans 602 and 604 in feature scan 502.

Registration locates point B in feature map 606 relative to point A by determining the position of patch image 402 within baseline image 404. Prior to the registration of a patch image such as patch image 402 to a baseline image such as baseline image 404, as illustrated in FIG. 4, the landmarks (e.g. blood vessels or other features) of patch image 402 and of baseline image 404 are processed to rectify their displacements due to eye motion. For example, due to eye motion, the blood vessels in patch image 402 and/or baseline image 404 can become distorted or discontinued. Applying a thinning (skeletonization) algorithm followed by an edge-tracing operation to each image, the amount of displacement ($\Delta x, \Delta y$) at the distorted or discontinued locations can be obtained and corrected. Then, the rectified patch image is registered in the rectified baseline image. Image processing techniques such as matching and autocorrelation can be utilized in the fulfillment of a registration to align the landmarks of patch image 402 with the correspondingly identical landmarks of baseline image 406. In some embodiments of the present invention, high-performance computing hardware and techniques, such as the hardware-related Streaming SIMD (Single Instruction Multiple Data) Extension (SSE), can be used to increase the speed of performing a registration of patch image 402 with baseline image 404. In some embodiments, processing of the data may be accomplished on external computing systems.

As mentioned earlier, features found in the feature map, such as feature map 606, are important in the assessment of many macular diseases. For example, an Early Treatment Diabetic Retinopathy Study (ETDRS) chart, which is usually centered on the fovea, is commonly used for the diagnosis of diabetic retinopathy. As shown in feature map 606 of FIG. 6, the fovea (point C) may be identified by detecting the dips in thickness along the horizontal-scanned and vertical-scanned OCT images. However, the positional information of the fovea cannot often be obtained correctly, especially for patients of severe retinal edema. The positional information may need to be adjusted by experienced clinicians. However, once this is done for a particular patient, the adjusted positional information can be recorded together with baseline image 404, as described in the next step, and utilized in subsequent scans. Therefore, in some embodiments of the invention, positional information may be adjusted by a clinician prior to storing the data.

After the fovea (point C) has been identified, its positional information within baseline image 404 can be computed and recorded. First, the relative position between point B and point C in feature map 606 is readily obtained. Then, the fovea location, point C in feature map 606, within baseline image 404 can be obtained by simple coordinate transformations, taking into account possible differences in the scan resolutions. Consequently, when a patient has another examination with a scan pattern such as scan pattern 500 shown in FIG. 5, the registration methods can be utilized to compute the new point location B with respect to a probably different point A (aiming center) in feature map 606. Because the positional information of the fovea has been recorded within baseline image 404, the fovea location in the newly generated feature map 606 is readily obtained, again, by simple coordinate transformations.

A baseline image can also be used for the examination of the optic nerve head. Once acquired, the baseline image is saved and used for further studies such as a progressive analyses. A pattern such as scan pattern 300 shown in FIG. 3 may be utilized to acquire a sequence of OCT images, wherein the scan pattern substantially covers the eye features of interest, for examples, the optic disc center. However, other scan patterns can be utilized for both baseline, feature, and patch scans.

Figure 7:
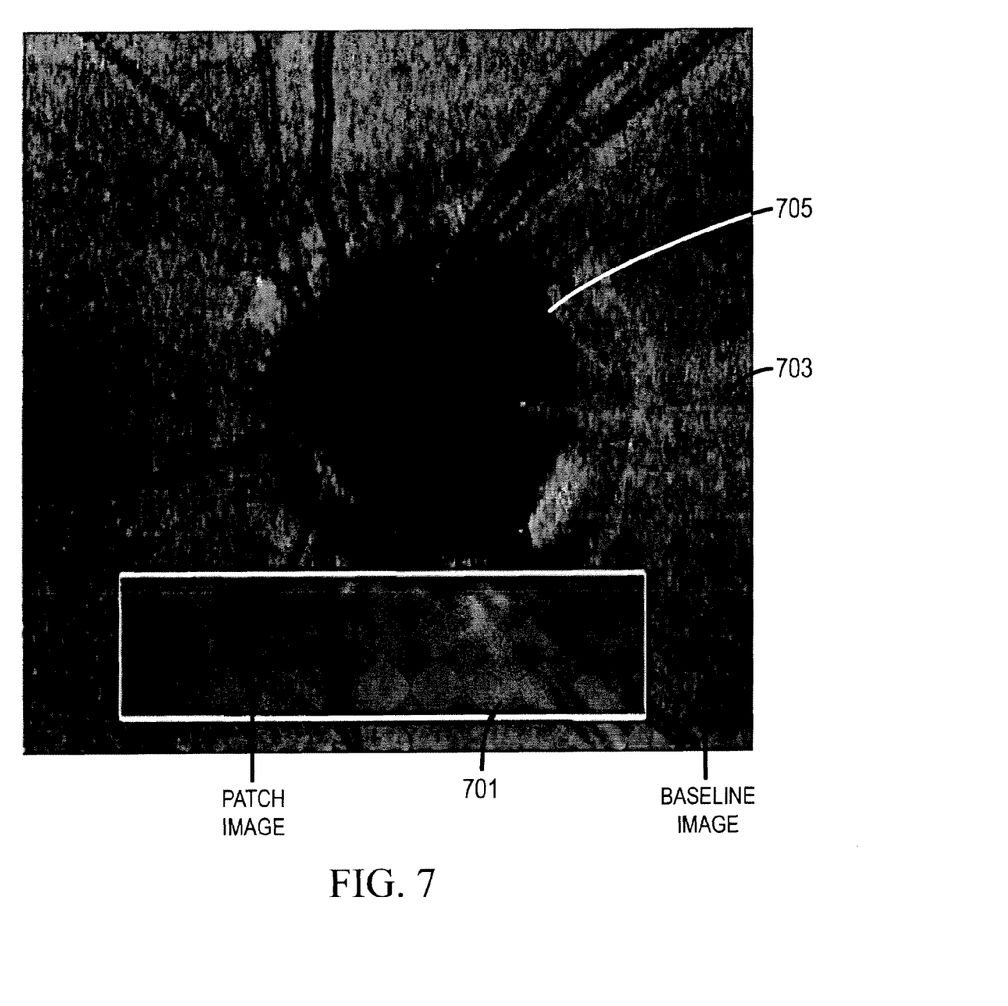
FIG. 7 illustrates registration of another sample patch image within another sample baseline image.
Figure 8:
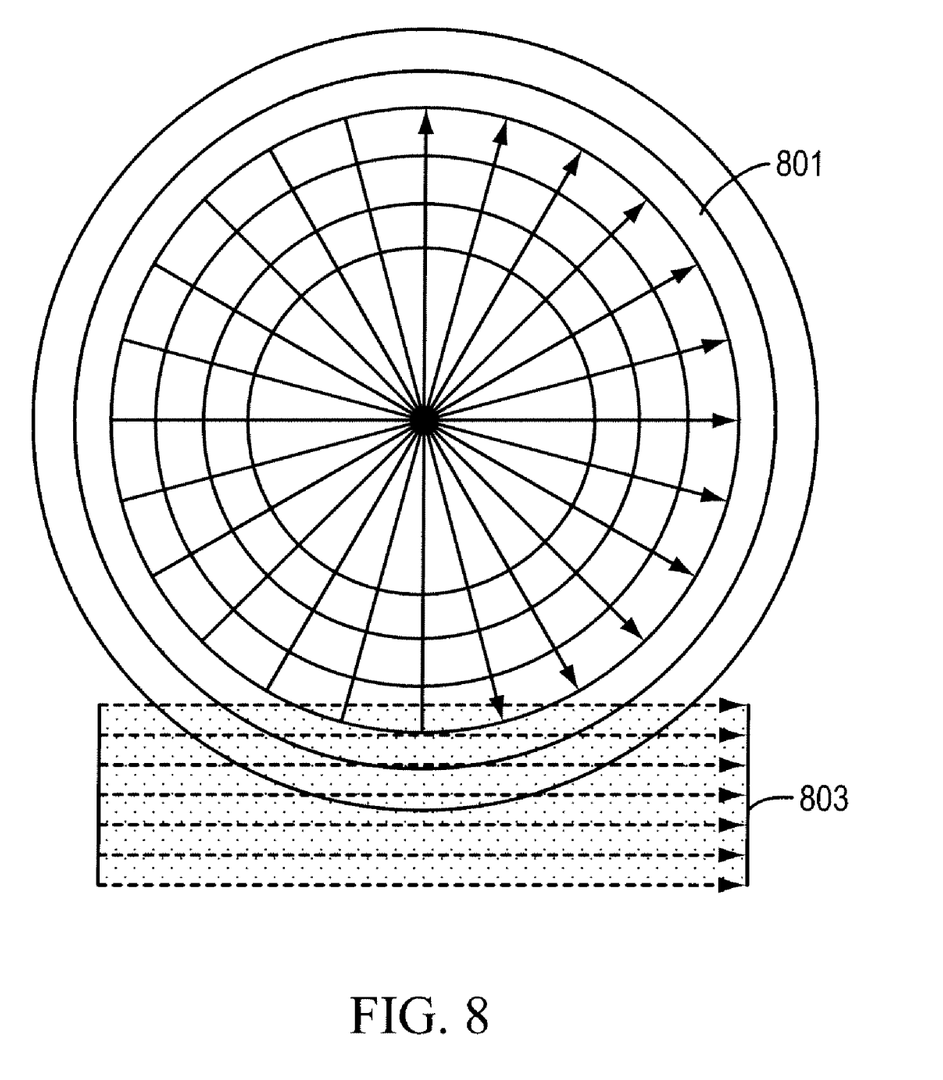
FIG. 8 shows another example scan pattern that includes feature scans and patch scans that can be utilized to acquire a sequence of OCT images.

FIG. 7 illustrates registration of a patch image 701 within a sample baseline image 703 that includes an optic disc center 705. Baseline image 703 is generated from baseline scan pattern 801 as shown in FIG. 8. Patch image 701 is formed from patch scan pattern 803 as shown in FIG. 8.

FIG. 8 shows scan pattern 800, which can be utilized to acquire a sequence of OCT images, wherein the scan pattern substantially covers a nerve head region 705. Scan pattern 801 (designated by solid lines) can be utilized for forming baseline image 703. Further, scan pattern 801 can be utilized to obtain feature scans. Scan pattern 803 (designated by dashed lines) are patch scans. As discussed above, feature scans are utilized to generate a feature map whereas patch scans are utilized for generating a patch image to be used for registration against baseline image 703. As shown in FIG. 8, scan pattern 801 is a radial scan.

Again, baseline image 703 can be generated similar to an enface image and is composed by summing all or partial tissue reflectivity of the scanned OCT images. Features such as retinal blood vessels can be enhanced and can be utilized as landmarks to help with registration.

Figure 9:
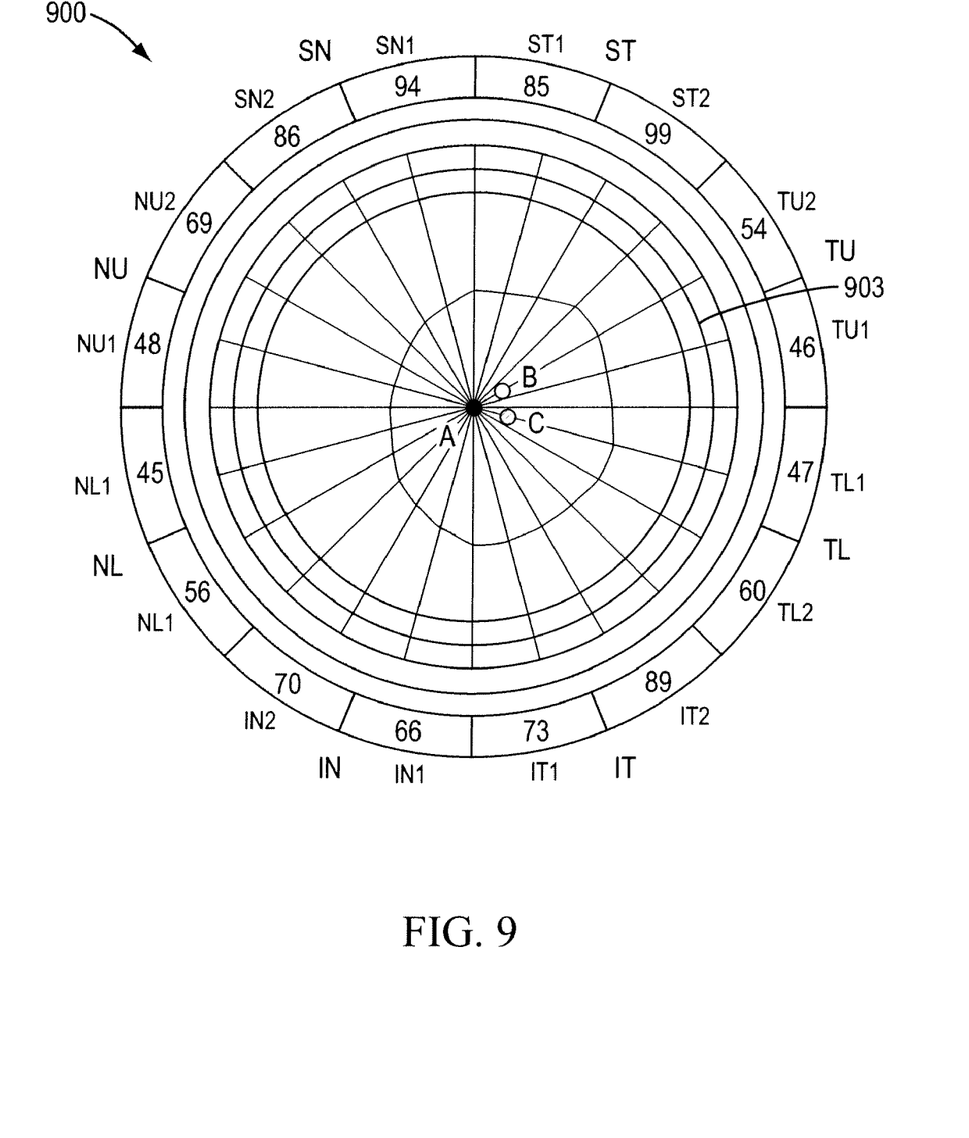
FIG. 9 shows a schematic illustrating generation of a feature map, identification of features on the feature map, and recording positional information of features consistent with some embodiments of the present invention.

FIG. 9 shows a schematic picture illustrating the steps of generating a feature map, identifying features in the feature map, and recording the positional information of features in the present invention. Retinal thickness, measured from the ILM to the retinal nerve fiber layer (RNFL), as discussed above, can be used as a feature for registration. Retinal thickness can be an important feature because thinning in the RNFL thickness may be a powerful indicator of neurodegenerative diseases such as glaucoma. An important location to measure retinal thinning is directly related to the optic disc center, which is indicated at point C in feature map 900 shown in FIG. 9. As shown in the particular example illustrated in feature map 900, the thinning in the area of radius 1.725 mm from the optic disc center can have a profound effect on visual acuity.

In the feature map shown in FIG. 9, the radii of the circle scans 903 shown are 1.25 mm, 1.40 mm, 1.55 mm, 1.70 mm, 1.85 mm, and 2.00 mm, respectively. The feature map is also segregated into areas, including the ST: Superior Temporal, TU: Temporal Upper, TL: Temporal Lower, IT: Inferior Temporal, IN: Inferior Nasal, NL: Nasal Lower, NU: Nasal Upper, and SN: Superior Nasal areas. In some cases, feature map 900 may be color coded to show thickness. This type of measurement can be particular useful in tracking patients with glaucoma. For example, the average thickness values around the radius 1.725 mm from the optic disc center are represented by 16 sectional data as $ST1=85$, $ST2=99$, ... $SN1=94$, respectively, in FIG. 9. From these measurements, physicians not only can obtain the global thinning information but also the local thinning information (the most deteriorated region). As a consequence, the determination of the optic disc center and its accuracy become critical, especially for progression analyses.

As discussed above, FIG. 8 illustrates a scan pattern 800 to acquire a sequence of OCT images that includes feature scans 801 (solid lines) to generate the feature map for diagnosis, and patch scans 803 (broken lines) for generating a patch image to be used for registration baseline image 703. Baseline image 703 may also be acquired from scan 801.

Patch image 701 can be generated similar to baseline image 703 as described above. Feature map 900 is generated from feature scans 801 in FIG. 8, typically utilizing 2D interpolation techniques. Point A indicates the aiming center of the scan pattern 801, point B the aiming center of the baseline scan pattern resulting in baseline image 703, and point C the feature location, in this example the optic disc center, in feature map 900.

A registration method locates point B in FIG. 9 relative to point A. Prior to registration of patch image 701 to baseline image 705 as shown in FIG. 7, the landmarks (e.g. blood vessels) of patch image 701 and baseline image 703 are processed to rectify displacements due to eye motion. For example, due to eye motion, the blood vessels in patch image 701 and/or baseline image 703 can become distorted or discontinued. Applying a thinning (skeletonization) algorithm followed by an edge-tracing operation to each image, the amount of displacements ($\Delta x$, $\Delta y$) at the distorted or discontinued locations can be obtained and utilized to correct the distortion. Then, the rectified patch and rectified baseline images are used for the registration. Image processing techniques such as image alignment and autocorrelation can be utilized to match patch image 701 with baseline image 703. As before, high-performance computing techniques, such as the hardware-related Streaming SIMD (Single Instruction Multiple Data) Extension (SSE), may be utilized to increase the speed of performance, or the images may be evaluated at a later time on an external system.

As mentioned earlier, features in feature map 900 can be important in the assessment of many macular diseases. For example, a RNFL 3.45 mm profile chart is commonly used for the diagnosis of glaucoma. This chart is centered at the optic disc center with a radius=1.725 mm. As shown in FIG. 9, the optic disk center (point C) may be identified by detecting the disc boundaries along the circle-scanned and radial-scanned OCT images resulting from scan 801. However, the positional information of the optic disc center cannot often be obtained correctly, especially for patients with severe macular diseases. The positional information may be adjusted by experienced clinicians and those adjustments recorded together with baseline image 703.

After the optic disc center (point C) has been identified, its positional information within baseline image 703 can be computed and recorded. First, the relative position between point B and point C in feature map 900 is readily obtained. Then, the optic disc center location within baseline image 703 can be obtained by simple coordinate transformations, taking into account possible differences in the scan resolutions. Consequently, when a patient has another examination with a scan pattern such as scan pattern 800 of FIG. 8, the disclosed registration methods compute the new point location B with respect to a probably different point A (aiming center) in feature map 900. Because the positional information of the optic disc center has been recorded within baseline image 703, the optic disc center location in the newly generated feature map is readily obtained, again, by simple coordinate transformations.

In the above embodiments, a patch image may or may not be overlapped with the region corresponding with the feature map. In some embodiments, as shown in procedure 251 of FIG. 2B, no patch image or baseline image are used. Instead, additional feature scans are used to increase the scanning density such that registration can be reliably performed against images formed from the feature scans. In other words, all the scans can be utilized in generating a feature map.

Figure 10:
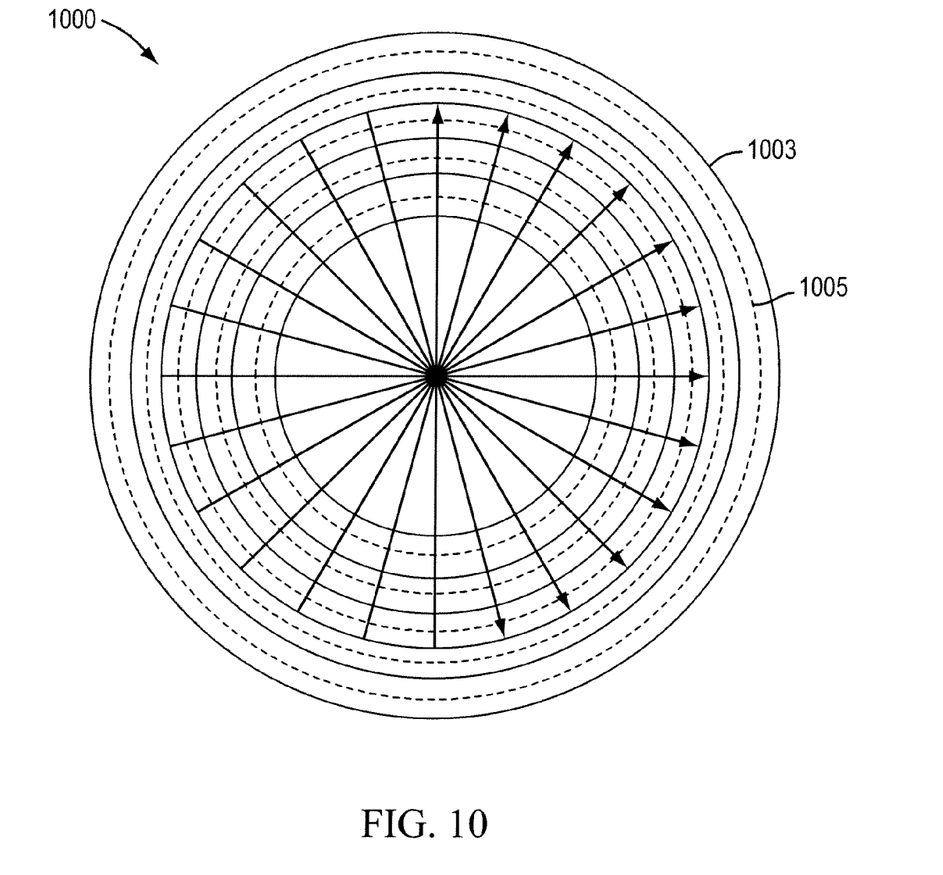
FIG. 10 shows a scan pattern to acquire a sequence of OCT images that includes original feature scans and additional feature scans for generating a registered feature map without utilizing a baseline image and a patch image.

FIG. 10 shows a scan pattern 1000 to acquire a sequence of OCT images that may be utilized in procedure 251. Scan pattern 1000 includes original feature scans 1003 corresponding to solid lines and additional feature scans 1005 corresponding to broken lines. Feature scans 1003 and additional feature scans 1005 can be utilized to generate a registered feature map such as those shown in FIGS. 9 and 6 without using either a baseline image or a patch image. The additional feature scans 1005 can be utilized for registration. The additional scans are within the region covering the feature map, and thus all the scanned images contribute to generation of the feature map.

Based on all of feature scans 1000, a 2D or 3D intensity image, a simulated scanning laser ophthalmoscope (SSLO) image, can be generated, similar to an enface image, by summing all or partial tissue reflectivity of the scanned OCT images. Features such as the retinal blood vessels can be enhanced and utilized as landmarks for registration. The generated image is similar to baseline image 703 shown in FIG. 7.

Further, feature map 900 based on feature scans 1000 can be created. A registration method to locate point B relative to point A in feature map 900 is similar to that described with FIG. 9, except that point B now corresponds to the aiming point of a previously obtained feature map. Prior to registration of two SSLO images, the landmarks (e.g. blood vessels) of the two SSLO images are processed to rectify their displacements due to eye motion. Then, the rectified SSLO images are used for the registration. Image processing techniques such as alignment and autocorrelation, can be utilized to align the two SSLO images. High-performance computing techniques, such as the hardware-related Streaming SIMD (Single Instruction Multiple Data) Extension (SSE), can be used to increase the speed of performance.

As mentioned earlier, features in the feature map are important in the assessment of many macular diseases. For example, a RNFL 3.45 mm profile chart is commonly used for the diagnosis of glaucoma. This chart is centered at the optic disc center. As shown in FIG. 9, the optic disk center (point C) may be identified by detecting the disc boundaries along the circle-scanned and radial-scanned OCT images. However, the positional information of the optic disc center cannot often be obtained correctly, especially for patients of severe macular diseases. The positional information may need to be adjusted by experienced clinicians and the positional information recorded together with the baseline image, as described in the next step.

After the optic disc center (point C) has been identified, its positional information within the baseline image can be computed and recorded. First, the relative position between point B and point C in feature map 900 is readily obtained. Then, the optic disc center location within the baseline image can be obtained by simple coordinate transformations due to possible differences in the scan resolutions. Consequently, when a patient has another examination with a scan pattern like scan 1000 in FIG. 10, the disclosed registration methods compute the new point location B with respect to a probably different point A (aiming center) in the feature map. Since the positional information of the optic disc center has been recorded within the baseline image, the optic disc center location in the newly generated feature map is readily obtained, again, by simple coordinate transformations.

Formation of a baseline image from baseline scans, patch image from patch scans, or feature images from feature scans can include any number of image enhancement techniques. Such techniques include image enhancement, smoothing, and motion detection and correction. Further, matching one image to another, as is performed when a patch image is registered to a background image or a feature image is registered to previously obtained feature images, may also be undertaken. These image manipulation techniques can be undertaken on computer 108 as shown in FIG. 1 for display to an operator on a display, which is part of computer 108. Alternatively, data from scanner 100 shown in FIG. 1 may be downloaded to another computer for ultimate data analysis.

In some embodiments of the invention, features can be identified automatically by analyzing images formed from the scan. For example, the fovea as a feature may be detected by locating the minimum in the thickness map representing the distance between the retinal ILM layer to the IPL layer or the RPE layer. As another example, the optic disc center can be identified by locating the optic disc boundary in an image that includes the optic disk and computing the geometric center of the disc boundary. The optic disc boundary, for example, can be determined in an enface image taken along with the OCT scans.

Several embodiments of the invention have been disclosed above. It should be understood that the these embodiments are examples of the invention only and are not meant to be limiting. Numerous rearrangements and modifications of parts and elements can be made without departing from the spirit of the invention. As such, the invention is limited only by the following claims.

What is claimed is:

1. A method of eye registration, comprising:
    performing a baseline pattern scan, wherein acquiring a baseline pattern scan comprises performing scans of an eye in one or more directions to acquire a sequence of optical coherence tomography (OCT) images;
    generating a baseline image from the baseline pattern scan, wherein generating a baseline image comprises summing all or partial tissue reflectivity of the acquired OCT images;
    acquiring scan pattern scans;
    forming images from the scans;
    registering the images;
    generating a feature map from the scan pattern scans;
    identifying features on the feature map; and
    recording positional information of features.

2. The method of claim 1, wherein forming images from the scans includes forming a patch image.

3. The method of claim 2, wherein registering the images includes matching the patch image with a corresponding portion of the baseline image.

4. The method of claim 1, wherein registering the images includes registering against previously obtained scan pattern scans.

5. The method of claim 1, wherein acquiring scan pattern scans includes acquiring both a feature scan and a patch scan.

6. The method of claim 5, wherein generating a feature map includes forming an image from the feature scan.

7. The method of claim 1, wherein acquiring scan pattern scans includes acquiring a feature scan and an additional feature scan.

8. The method of claim 7, wherein generating a feature map includes forming an image from the feature scan and wherein registering scan pattern images includes registering images formed from the additional feature scan with previously taken feature scan images.

9. The method of claim 1, wherein the feature map represents features in thickness measurements from the retinal inner limiting membrane (ILM) to the retinal pigment epithelium (RPE) layer, or from the retinal ILM to the retinal nerve fiber layer (RNFL) layer.

10. The method of claim 1, wherein registering the images includes 2D enface and 3D optical coherence tomography (OCT) images processing steps.

11. The method of claim 10, wherein the 2D enface and 3D OCT images processing steps includes image enhancement.

12. The method of claim 10, wherein the 2D enface and 3D OCT images processing steps include smoothing.

13. The method of claim 10, wherein the 2D enface and 3D OCT images processing steps include motion detection.

14. The method of claim 10, wherein the 2D enface and 3D OCT images processing steps include image matching.

15. The method of claim 10, wherein the 2D enface and 3D OCT images processing steps include thinning and edge-tracing.

16. The method of claim 1, wherein identifying features includes locating the minimum in the thickness map representing the distance between the retinal ILM layer to the IPL layer or the RPE layer.

17. The method of claim 1, wherein identifying features includes locating an optic disc boundary and determining an optic disc center by determining a geometric center of the optic disc boundary.

18. The method of claim 17, wherein the optic disc boundary is obtained from the enface image formed along with the scanned OCT images.

19. The method of claim 1, wherein the scan pattern scans are processed to generate a simulated scanning laser ophthalmoscope (SSLO) image and wherein registering the image includes registering SSLO images.

20. The method of claim 19, wherein registering SSLO images includes registering the SSLO image against another previously generated SSLO image.

21. The method of claim 1, further comprising:
    applying a thinning algorithm followed by an edge-tracing operation to the baseline image and the images to correct distorted or discontinued locations.

* * * * *